US012023113B2

(12) United States Patent
Prisco et al.

(10) Patent No.: US 12,023,113 B2
(45) Date of Patent: Jul. 2, 2024

(54) METHOD AND SYSTEM FOR OPERATING A TELEOPERATED SURGICAL INSTRUMENT AND A MANUAL INSTRUMENT

(71) Applicant: INTUITIVE SURGICAL OPERATIONS, INC., Sunnyvale, CA (US)

(72) Inventors: Giuseppe Maria Prisco, Calci Pisa (IT); Myriam J. Curet, Los Altos, CA (US); Vincent Duindam, San Francisco, CA (US); Catherine J. Mohr, Mountain View, CA (US); Theodore W. Rogers, Alameda, CA (US); Katherine D. Stoy, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 174 days.

(21) Appl. No.: 17/575,541

(22) Filed: Jan. 13, 2022

(65) Prior Publication Data
US 2022/0211450 A1 Jul. 7, 2022

Related U.S. Application Data

(60) Division of application No. 16/788,045, filed on Feb. 11, 2020, now Pat. No. 11,252,141, which is a
(Continued)

(51) Int. Cl.
*A61B 34/30* (2016.01)
*A61B 17/24* (2006.01)
(Continued)

(52) U.S. Cl.
CPC .............. *A61B 34/30* (2016.02); *A61B 17/24* (2013.01); *A61B 34/20* (2016.02); *A61B 34/71* (2016.02);
(Continued)

(58) Field of Classification Search
CPC . A61B 34/30; A61B 34/20; A61B 2034/2061; A61B 1/009; A61B 17/24;
(Continued)

(56) References Cited

U.S. PATENT DOCUMENTS 4,178,069 A 12/1979 Andersen et al.
4,373,779 A 2/1983 Dorsey
(Continued)

FOREIGN PATENT DOCUMENTS

JP 2001275931 A 10/2001
JP 2003515104 A 4/2003
(Continued)

OTHER PUBLICATIONS

Duncan, Roger G. et al., "Characterization of a Fiber-Optic Shape and Position Sensor," Proc. of SPIE, 2006, pp. 616704-1-616704-11, vol. 6167, SPIE.
(Continued)

*Primary Examiner* — Scott Luan
(74) *Attorney, Agent, or Firm* — Haynes and Boone, LLP

(57) ABSTRACT

A system comprises a teleoperated manipulator, a manually operated instrument, and a position sensor coupled to the manually operated instrument. The position sensor is configured to generate pose information for the manually operated instrument. The system further comprises a controller configured to map a pose of the manipulator to a fixed world reference frame based on three-dimensional pose information for the manipulator known internally within the system. The controller is further configured to map a pose of the
(Continued)

manually operated instrument to the fixed world reference frame based on the pose information for the manually operated instrument.

21 Claims, 7 Drawing Sheets

Related U.S. Application Data division of application No. 15/014,559, filed on Feb. 3, 2016, now Pat. No. 10,588,703, which is a continuation of application No. 12/839,642, filed on Jul. 20, 2010, now Pat. No. 9,285,246.

(60) Provisional application No. 61/304,094, filed on Feb. 12, 2010.

(51) Int. Cl.
| | | |
|---|---|---|
| *A61B 34/00* | (2016.01) | |
| *A61B 34/20* | (2016.01) | |
| *G01B 11/24* | (2006.01) | |
| *G01D 5/353* | (2006.01) | |
| *H04L 9/40* | (2022.01) | |
| *H04W 4/80* | (2018.01) | |
| *H04W 12/06* | (2021.01) | |
| *A61B 18/00* | (2006.01) | |
| *A61B 18/20* | (2006.01) | |

(52) U.S. Cl.
CPC ......... *G01B 11/24* (2013.01); *G01D 5/35316* (2013.01); *H04L 63/0428* (2013.01); *H04L 63/08* (2013.01); *H04L 63/0807* (2013.01); *H04W 4/80* (2018.02); *H04W 12/06* (2013.01); *H04W 12/068* (2021.01); *A61B 2018/00035* (2013.01); *A61B 2018/2005* (2013.01); *A61B 2018/202* (2013.01); *A61B 2034/2061* (2016.02); *A61B 2034/301* (2016.02); *A61B 2562/00* (2013.01)

(58) Field of Classification Search
CPC .. A61B 2018/00035; A61B 2018/2005; A61B 2018/202; A61B 2034/301; A61B 2562/00; A61B 34/71; G01D 5/35316; G01B 11/24; H04L 63/0428; H04L 63/08; H04L 63/0807; H04W 12/06; H04W 12/068; H04W 4/80
USPC .......... 385/12, 13; 606/1, 130; 600/117, 424
See application file for complete search history.

(56) References Cited

U.S. PATENT DOCUMENTS

| | | | |
|---|---|---|---|
| 5,353,798 A | 10/1994 | Sieben | |
| 5,798,521 A | 8/1998 | Froggatt | |
| 6,389,187 B1 | 5/2002 | Greenaway et al. | |
| 6,471,710 B1 | 10/2002 | Bucholtz | |
| 9,285,246 B2 | 3/2016 | Prisco et al. | |
| 10,028,791 B2 * | 7/2018 | Prisco | A61B 34/71 |
| 10,588,703 B2 * | 3/2020 | Prisco | H04L 63/0807 |
| 10,687,907 B2 | 6/2020 | Prisco et al. | |
| 11,252,141 B2 * | 2/2022 | Prisco | G01B 11/24 |
| 2004/0165810 A1 | 8/2004 | Fujita | |
| 2006/0013523 A1 | 1/2006 | Childlers et al. | |
| 2007/0142749 A1 | 6/2007 | Khatib et al. | |
| 2007/0156019 A1 | 7/2007 | Larkin et al. | |
| 2007/0249901 A1 | 10/2007 | Ohline et al. | |
| 2007/0287992 A1 | 12/2007 | Diolaiti et al. | |
| 2008/0212082 A1 | 9/2008 | Froggatt et al. | |
| 2008/0218770 A1 | 9/2008 | Moll et al. | |
| 2008/0287963 A1 | 11/2008 | Rogers et al. | |
| 2009/0137952 A1 | 5/2009 | Ramamurthy et al. | |
| 2009/0192355 A1 | 7/2009 | Mejia | |
| 2009/0324160 A1 | 12/2009 | Rogers et al. | |
| 2009/0324161 A1 | 12/2009 | Prisco | |
| 2010/0030063 A1 | 2/2010 | Lee et al. | |
| 2010/0099951 A1 | 4/2010 | Laby et al. | |
| 2011/0113852 A1 | 5/2011 | Prisco | |
| 2011/0119023 A1 | 5/2011 | Duindam et al. | |
| 2011/0164846 A1 | 7/2011 | Zhang et al. | |
| 2015/0157410 A1 | 6/2015 | Kilroy et al. | |
| 2020/0267128 A1 | 8/2020 | Prisco et al. | |

FOREIGN PATENT DOCUMENTS

| | | |
|---|---|---|
| JP | 2008190910 A | 8/2008 |
| WO | WO-0133165 A1 | 5/2001 |
| WO | WO-2005084542 A1 | 9/2005 |
| WO | WO-2009023801 A1 | 2/2009 |

OTHER PUBLICATIONS

Luna Technologies Inc., User Guide for Optical Backscatter Reflectometer, Version 1.0 for OBR control software version 0.42 Beta, Chapters 5 and 6, pp. 33-60, 2004.
Office Action dated Sep. 24, 2014 for Japanese Application No. JP20120552896 filed Jan. 28, 2011.
PCT/US11/22823 International Search Report and Written Opinion of the International Searching Authority, dated May 2, 2011, 11 pages.
Rice, Trevor, "NASA-Inspired Shaped-Sensing Fibers Enable Minimally Invasive Surgery," 2 pages, posted Feb. 1, 2008, Internet: http://www.techbriefs.com/content/view/2585.
Shigenkuni S., et al., "Synthesis of Fluorinated Polyimides," in: Ghosh, Malay & K.L. Mittal, Polyimides: Fundamentals and Applications (New York, Marcel Dekker, Inc.,) 1996, pp. 71.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

METHOD AND SYSTEM FOR OPERATING A TELEOPERATED SURGICAL INSTRUMENT AND A MANUAL INSTRUMENT

RELATED APPLICATION

This application is a divisional of U.S. patent application Ser. No. 16/788,045, filed Feb. 11, 2020, which is a divisional of U.S. patent application Ser. No. 15/014,559, filed Feb. 3, 2016, now U.S. Pat. No. 10,588,703, which is a continuation of U.S. patent application Ser. No. 12/839,642, filed Jul. 20, 2010, now U.S. Pat. No. 9,285,246, which claims priority to and the benefit of U.S. Provisional Application No. 61/304,094, filed Feb. 12, 2010, and entitled "METHOD AND SYSTEM FOR ABSOLUTE THREE-DIMENSIONAL MEASUREMENTS USING A TWIST-INSENSITIVE SHAPE SENSOR," naming as inventors, Giuseppe M. Prisco, Theodore W. Rogers, Vincent Duindam, Myrian J. Curet, Catherine J. Mohr, Katherine D. Stoy, all of which are incorporated herein by reference in their entireties.

BACKGROUND

Field of Invention

Aspects of this invention are related to sensing information to characterize a minimally invasive surgical instrument, and more particularly to shape sensors used to obtain shape information and absolute three-dimensional pose information for the minimally invasive surgical instrument.

Related Art

A recurring problem in minimally invasive surgery is determining the pose and/or shape of an instrument used in the surgery. Also, determining anatomical locations in a patient and correlating MRI images, or other images to images of the patient taken during surgery requires three-dimensional measurements.

Current methods used to obtain shape information about a flexible surgical instrument include camera and vision based methods, inertial and gyroscopic sensors based methods, and electromagnetic field sensor based methods. Also, there are mechanical systems that can touch two different locations and determine the relative relationships between the two locations.

These methods are limited in sensing precision and accuracy, sensitivity to environmental conditions, invasiveness in practical application, and can generally only provide position information on a certain discrete number of points on the surgical instrument. Also, the distances measured are relative distances and not absolute distances.

Optical fiber shape sensors are known. See e.g., U.S. Pat. No. 5,798,521 (filed 27 Feb. 1997), U.S. Pat. No. 6,389,187 B1 (filed 17 Jun. 1998), U.S. Patent Application Pub. No. US 2006/0013523 A1 (filed 13 Jul. 2005), and Roger G. Duncan et al., Characterization of a Fiber-Optic Shape and Position Sensor, Smart Structures and Materials 2006: Smart Sensor Monitoring Systems and Applications (D. Inaudi et al. eds.), 6167 Proceedings of SPIE 616704 (16 Mar. 2006), all of which are incorporated by reference. Optical fiber shape sensors have been used to sense joint angles in a minimally invasive surgical instrument. See, e.g., U.S. Patent Application Pub. No. US 2007/0156019 A1 (filed 20 Jul. 2006) and NASA Tech Briefs, NASA-Inspired Shape-Sensing Fibers Enable Minimally Invasive Surgery (1 Feb. 2008), http://www.techbriefs.com/content/view/2585/, both of which are incorporated herein by reference.

Typically, optical fiber shape sensors operate via optical time domain reflectometry (OTDR) or via optical frequency domain reflectometry (OFDR). Most approaches use a backscatter method that measures changes in backscattered light caused by a change in the shape of the optical fiber. Scattering mechanisms that have been used include Rayleigh scattering, Raman scattering, Brillouin scattering, and Fluorescence scattering. Fiber Bragg Gratings and the Kerr effect have also been used in shape-sensing sensors. Some of the Fiber Bragg Grating shape sensors are insensitive to twist. Consequently, if the shape sensor is twisted, the pose information obtained using the twisted shape sensor is not correct.

Other techniques have also been used for shape sensing. For example, electromagnetic fields have been used in combination with sensors mounted on an endoscope to determine a position of an endoscope. See U.S. Patent Application Publication No. 2007/0249901 A1 (filed Mar. 28, 2006; disclosing "Instrument Having Radio Frequency Identification Systems and Methods for Use."), which is incorporated herein by reference in its entirety. Also, the changes in resistance of a piezoresistive flexible shape sensor have been used to measure shape changes.

SUMMARY

In one aspect, an apparatus includes a reference fixture. The reference fixture includes a joint, and, in one aspect, a joint tracker to track motion of the joint. The apparatus also includes a surgical instrument. A tether is connected between the joint and the surgical instrument. A shape sensor extends from the reference fixture through the joint, through the tether, and into the surgical instrument. The shape sensor is substantially free of twist.

Information from the shape sensor in combination with information from the joint tracker provides absolute three-dimensional information relative to the reference fixture, i.e., provides absolute three-dimensional information in a fixed world reference frame. This absolute three-dimensional information in a fixed world reference frame contrasts with information from conventional methods that provide relative distances between elements of a surgical instrument, relative distances between surgical instruments, or a relative distance between locations in a patient undergoing the medical procedure.

The ability to obtain absolute three-dimensional shape and pose data in a fixed world reference frame provides a new level of capability in medical procedures. In addition, the absolute three-dimensional pose data (position and orientation) in the world fixed reference frame permits registering various images, for example, in the world fixed reference frame and superimposing the images as needed to facilitate a more informed surgical process.

In one aspect, the joint has only one degree of freedom. For example, the joint is a roll joint and the one degree of freedom is roll. In another example, the joint includes a ball and screw joint. In another aspect, the joint has multiple degrees of freedom that include the one degree of freedom.

The number of degrees of freedom in the joint or combination of joints is selected to facilitate moving the surgical instrument by a surgeon. The torsionally stiff tether between the surgical instrument and the reference structure may inhibit manipulation of the surgical instrument by the surgeon. Thus, a joint or a combination of joints is used in the reference structure to facilitate manipulation of the surgical instrument thru all degrees of freedom of the surgical instrument. In aspects where manipulation of the surgical instrument is not inhibited by the tether, or the inhibition is not significant in use of the surgical instrument, a joint with zero degrees of freedom may be used in the reference structure and the joint tracker is not needed.

The tether defines a lumen extending along a longitudinal axis of the tether, and the shape sensor extends through the lumen. In one aspect, the tether is torsionally stiff.

In another aspect, a liner extends through the lumen in the tether. The liner includes a liner lumen and the shape sensor extends through the liner lumen. The liner is made from a material such that the shape sensor rotates freely within the liner. In one aspect the material is a fluorinated polymer.

In another aspect, a processor processes information, from a joint tracker connected to a reference fixture, to generate a first pose. The joint tracker measures motion of a joint connected to the tether. The tether couples the joint to a surgical instrument. The reference fixture is affixed to a location to define a fixed world reference frame for minimally invasive surgery.

The processor also processes information from a shape sensor extending through the joint and the tether to generate second pose information. The processor uses the first pose information and the second pose information to generate an absolute three-dimensional pose of a proximal part of the surgical instrument in the fixed world reference frame.

In one aspect, the shape sensor extends to a distal portion of the surgical instrument. The processor processes information from this segment of the shape sensor to generate third pose information. The processor uses the first pose information, the second pose information and the third pose information to generate an absolute three-dimensional pose of the distal portion of the surgical instrument in the fixed world reference frame. The processor also generates a shape of the surgical instrument in the fixed world reference frame.

In one aspect, the surgical instrument is a flexible surgical instrument such as an endoscope. In another aspect, the surgical instrument is a cannula. In yet another aspect, the surgical instrument is a snakelike robotic surgical instrument, which is one example of a flexible surgical instrument.

In another aspect, a method couples a surgical instrument to a distal end of a tether. A proximal end of the tether is coupled to a joint of a reference structure. The reference structure also includes a joint tracker that measures motion of the joint. This method extends a shape sensor through the joint and the tether into the surgical instrument. The shape sensor provides information for determining an absolute three-dimensional pose of a part of the surgical instrument relative to the reference structure.

In one aspect, the surgical instrument in this method is a cannula and the method also includes connecting the reference structure to an arm supporting a manipulator of a minimally invasive teleoperated surgical system.

Figure 1:
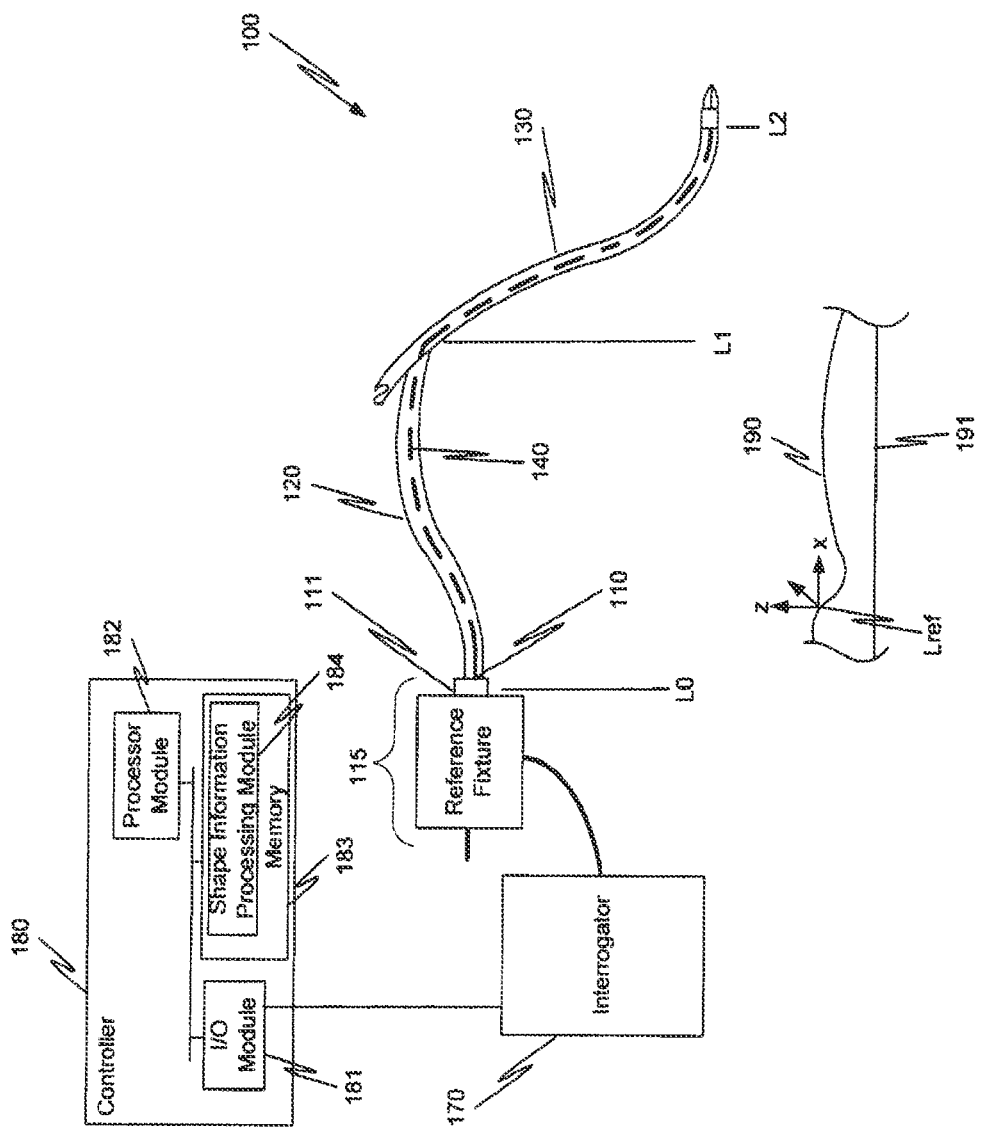
FIG. 1 is a diagrammatic view of a portion of a minimally invasive surgical system, which includes elements to generate absolute three-dimensional pose and shape data, in a fixed world reference frame, characterizing a surgical instrument.

In the drawings, the first digit of a reference number indicates the figure in which the element with that reference number first appeared.

DETAILED DESCRIPTION

Aspects of this invention include an apparatus 100 that in turn includes a combination of (1) a reference fixture 115 (FIG. 1) including a joint 110, and a joint tracker 111 to track motion of joint 110, and (ii) a shape sensor 140 to provide pose information of surgical instrument 130. Using information from joint tracker 111 and information from shape sensor 140, a processor module 182 generates an absolute three-dimensional shape of surgical instrument 130, and an absolute three-dimensional pose of surgical instrument 130 in a fixed world reference frame at location Lref.

As explained more completely below, location Lref for the fixed world reference frame can be fixed for a particular procedure at a location desired by the surgeon. For example, the fixed world reference frame at location Lref is fixed with respect to a patient undergoing surgery, is fixed with respect to a manipulator of a minimally invasive teleoperated surgical system, etc. In some procedures, location LO and location Lref could be the same location.

Typically, reference fixture 115 is mounted at a location LO. The relationship between a pose of location LO and the fixed world reference frame is known. Thus, controller 180 maps the pose of location LO to fixed world reference frame at location Lref.

In one aspect, after reference fixture 115 is fixed in position at location LO, location Lref is assigned to another location. For example, the fixed world reference frame at Lref is chosen to be at the mouth of patient 190 with x-axis and z-axis in the sagital plane of the patient, z-axis upward perpendicular to operating table 191, and x-axis aimed toward the feet of the patient. Then, in a registration step, a tip of surgical instrument 130 is used to touch several predetermined reference points on patient 190 and operating table 191. The processor uses the measured positions of these reference points relative to reference fixture 115 to compute the position and orientation of the frame at location LO relative to the fixed world reference frame Lref.

In this example, location Lref is at the mouth of the patient and the pose of location LO, which is the start of shape sending, is mapped into fixed world reference frame at location Lref. Thus, the absolute measurements described more completely below with respect to the reference frame at a location on reference fixture 115 are mapped to the fixed world reference frame at location Lref. Absolute measurements in the reference frame located at location LO in fixture 115, as described more completely below, are automatically mapped to absolute measurements in the fixed world reference frame at location Lref on the patient, in this example.

When the fixed world reference frame at location Lref is fixed with respect to the patient undergoing surgery, apparatus 100 provides absolute three-dimensional shape and pose data for surgical instrument 130 with respect to the patient. This absolute information contrasts with information from conventional methods that provide relative distances between elements of a surgical instrument, relative distances between surgical instruments, or a relative distance between locations in a patient undergoing the medical procedure.

The ability to obtain absolute three-dimensional shape and pose data in a fixed world reference frame provides a new level of capability in medical procedures. In addition, the absolute three-dimensional pose data (position and orientation) relative to the world fixed reference frame permits registering various images, for example, in the world fixed reference frame and superimposing the images as needed to facilitate a more informed surgical process.

In the aspect of FIG. 1, reference fixture 115 includes a joint 110 having at least one degree of freedom and a joint tracker 111. Reference fixture 115 is adapted to be affixed to a location of interest, e.g., a part of an operating table, a location on a minimally invasive teleoperated surgical system, etc. The means used to affix reference fixture 115 is any conventional means that securely attaches reference fixture to the desired location during use.

A tether 120 is connected between joint 110 of reference fixture 115 and surgical instrument 130. In one aspect, tether 120 has a proximal end connected to joint 110 in reference fixture 115. A distal end of tether 120 is connected to surgical instrument 130. Motion of the proximal end of tether 120 in the one degree of freedom results in motion of joint 110 in the one degree of freedom. Properties of tether 120 are described more completely below. The movement of joint 110 assists the surgeon in manipulating surgical instrument in the one degree of freedom, because joint 120 facilitates movement of tether 120 in that degree of freedom.

Motion of the proximal end of tether 120 is transferred to joint 110. Joint tracker 111 measures the motion of joint 110 and provides the information to controller 180. In this example, a joint with a single degree of freedom is considered, and in the example described more completely below, the joint is a roll joint.

The use of a joint with a single degree of freedom is illustrative only and is not intended to be limiting. As described more completely below, one or more degrees of freedom can be measured at the reference fixture. The use of a roll joint is also illustrative only. Another joint that could be used is a ball and screw joint. In view of this disclosure, those knowledgeable in the field can implement a joint or a combination of joints at the reference fixture, which have an appropriate number of degrees of freedom to facilitate the use of the surgical instrument while coupled to a tether.

Surgical instrument 130 can be any one of a number of different surgical instruments. For example, surgical instrument can be an instrument used in laparoscopic procedures, an instrument used in Natural Orifice Transluminal Endoscopic Surgery (NOTES) procedures, a cannula, a snake-like robotic surgical instrument, a probe used for establishing reference positions, or any flexible medical instrument used in a medical procedure for which absolute three-dimensional pose and shape information for that flexible medical instrument is useful.

In the aspect of FIG. 1, surgical instrument 130 is represented as a flexible surgical instrument having an end effector at the distal end. This is illustrative only and is not intended to limit surgical instrument 130 to only flexible surgical instruments.

A shape sensor 140 extends from reference fixture 115, thru joint 110 and joint tracker 111, through tether 120, and into surgical instrument 130 to a distal portion of surgical instrument 130. In the aspect of FIG. 1, shape sensor 140 is illustrated as passing through a lumen in each of reference fixture 115, joint 110 and joint tracker 111, tether 120, and surgical instrument 130. This is illustrative only and is not intended to be limiting to this specific example. In view of this disclosure, those knowledgeable in the field can position shape sensor 140 relative to reference fixture 115, thru joint 110 and joint tracker 111, through tether 120 and surgical instrument 130 to provide the necessary information to determine the absolute three-dimensional pose and shape of the surgical instrument being used.

In one example, shape sensor 140 is a shape-sensing optic fiber and Optical Frequency Domain Reflectometry is utilized in interrogator 170. In particular, a shape-sensing optic fiber utilizes Fiber Bragg Gratings. The use of Fiber Bragg Gratings is illustrative only and is not intended to be limiting to this specific mechanism for creating backscatter. In view of this disclosure, other optic fiber shape-sensing technologies could be used including but not limited to Rayleigh scattering, Raman scattering, and Brillouin scattering.

Further, the use of a shape-sensing optic fiber is also illustrative and is not intended to be limiting. For a particular type of shape sensor 140, an interrogator for that shape sensor is used. The data from the interrogator is processed using techniques equivalent to those described more completely below to obtain the absolute three-dimensional data. Accordingly, as stated previously, this example is illustrative of using a shape-sensing optic fiber to generate absolute three-dimensional pose information and is not intended to be limiting to the specific shape-sensing optic fiber described.

In one aspect, shape sensor 140 is implemented using a multi-core shape-sensing optic fiber. In one example, the optic fiber is a three core optic fiber, as described more completely below. In other embodiments, various numbers of cores may be used.

Interrogator 170 interrogates the optic fiber in shape sensor 140 and provides shape information to an input/output module 181 in controller 180. A processor in processor module 182 processes the information received by input/output module 181 using a shape information processing module 184.

Using information from joint tracker 111, the pose of the reference frame at location LO is determined. Note that, in this example, the position of the reference frame at location LO is fixed, but the orientation of the reference frame at location LO can change as joint 110 moves. Depending on the type of joint 110, different degrees of freedom in position and orientation of the reference frame at location LO change as the joint moves. The processor performs an integration, as described more completely below, using the information from shape sensor 140. The integration generates pose information for a frame at location Li in the reference frame at location LO. The processor combines this pose information with the pose of the reference frame at location LO to generate pose information for the frame at location LI in the fixed world reference frame at location Lref.

Similarly, integration of information from shape sensor 140 from location LO to location L2 generates pose information for a frame at location L2, in the reference frame at location L0. Combining this with the pose of reference frame at location L0 generates pose information for the frame at location L2 in the fixed world reference frame at location Lref. This integration also provides shape information of surgical instrument 130 between locations Li and L2 in fixed world reference frame at location Lref.

In this example, the initial position $(x_0, y_0, z_0)$ at location L0 is fixed and known and is mapped to the world fixed reference frame at location Lref. This initial position in the world fixed reference frame is used in the example described more completely below in offset vector $\bar{v}_0$ (See expression (17)). The orientation of the fixed world reference frame including the measurement from joint tracker 111 is used in coordinate system matrix $\bar{C}_0$, (See expression (9)).

A more detailed description of one process used to obtain coordinates $(x_n, y_n, z_n)$ at curvilinear coordinate L0+S1, i.e. at location L1, is described in copending and commonly assigned U.S. Patent Application Publication No. US 2009/0324161 A1, of U.S. Patent application Ser. No. 12/64,829, entitled "FIBER OPTIC SHAPE SENSOR," of Giuseppe M. Prisco, and filed on 30 Jun. 2008, which is incorporated herein by reference in its entirety.

Shape sensor 140 is fixed in position proximal to joint 110 and joint tracker 111. (Here, distal is away from joint 110 and joint tracker 111 towards surgical instrument 130 and proximal is the opposite direction.) Location L0 is typically at a center line of joint 100 in joint tracker 111 so that shape sensor 140 is fixed in position at a location removed from location L0, e.g., removed from the region being sensed.

Techniques and methods for fixing a shape-sensing optic fiber in position are described in commonly assigned U.S. patent application Ser. No. 12/164,297, entitled "FIXTURE FOR SHAPE-SENSING OPTICAL FIBER IN A KINEMATIC CHAIN," naming as inventors Theodore W. Rogers and Giuseppe Prisco, and filed on 30 Jun. 2008, which is incorporated herein by reference in its entirety. Also, conventional techniques for creating a service loop in an optic fiber that are used in the telecommunications industry could be used.

In one aspect, shape sensor 140 has a known feature, such as a known geometrical shape, at location L1 where shape sensor 140 enters surgical instrument 130. In one aspect, the distal end of shape sensor 140 in surgical instrument 130 is free to move.

Suitable techniques for implementing a known feature in shape sensor 140 at the proximal entry location in surgical instrument 130 are described in commonly assigned U.S. patent application Ser. No. 12/618,000, entitled "FIBER OPTIC SHAPE SENSOR," naming as inventor, Giuseppe M. Prisco, and filed on 13 Nov. 2009, which is incorporated herein by reference in its entirety. See also, commonly assigned U.S. patent application Ser. No. 12/618,082, entitled "Method and System to Sense Relative Partial-Pose Information Using a Shape Sensor," naming as inventors, Vincent Duindam et al., filed on 13 Nov. 2009, which is incorporated herein by reference in its entirety.

In one aspect, the known feature is an S-curve, in shape sensor 140 with a geometrical center at location L1. The lumen in which shape sensor 140 is located can be shaped to provide the known feature, or alternatively, a clamp or clamps on shape sensor 140 can be used to create the known feature.

The use of a known feature at the entry point of shape sensor 140 is optional. Alternatively, the length of the tether and the length of any distance in reference fixture 115 from location L0 to the proximal end of the tether can be measured to determine location L1. In some applications, location L1 is not of interest. Typically, for a flexible surgical instrument, the shape of the last half meter to meter of the distal end of the surgical instrument and the pose of the distal end of the surgical instrument are of interest.

In the aspect where shape sensor 140 is a multi-core shape-sensing optic fiber, care is taken to prevent shape sensor 140 from twisting in tether 120 and surgical instrument 130, because twisting distorts the measured shape information. In fact, in some conventional systems that relied only on a shape sensor to determine three-dimensional poses, the presence of twist resulted in inaccurate determinations.

In one aspect, twisting of shape sensor 140 (rotation about its tangential axis) is mitigated by using a torsionally stiff material for the body of tether 120 and for the body of surgical instrument 130. Suitable materials for the bodies include material used in endoscope bodies.

Herein, a torsionally stiff body is a body that has a twist smaller than a threshold while used in normal loading and normal use situations. The threshold is the amount of twist that would bother a surgeon while using surgical instrument 130 because the visual image of instrument 130 did not follow the motions made by the surgeon in manipulating surgical instrument 130 due to measurement error introduced by twisting of the shape sensor. Experiments have shown that a threshold of plus or minus ten degrees of twist is acceptable to most surgeons.

To further limit any twist of shape sensor 140, a torsionally stiff body can be used in combination with a lumen in the body having a non-circular cross section and a shape sensor having a same non-circular cross section. Such cross sections prevent the shape sensor from twisting within the lumen and so any twist is that imparted by the torsionally stiff body.

Figure 2A:
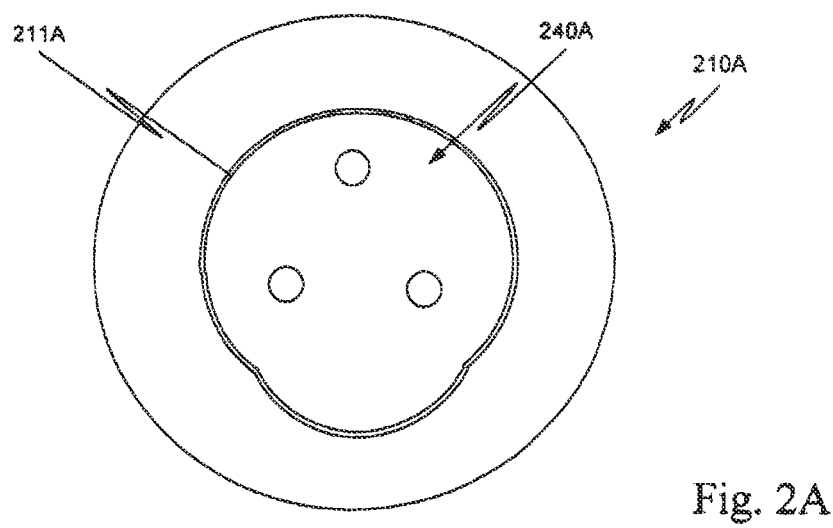
FIG. 2A is a cross sectional view of a tether and a shape sensor having a first non-circular cross section.
Figure 2B:
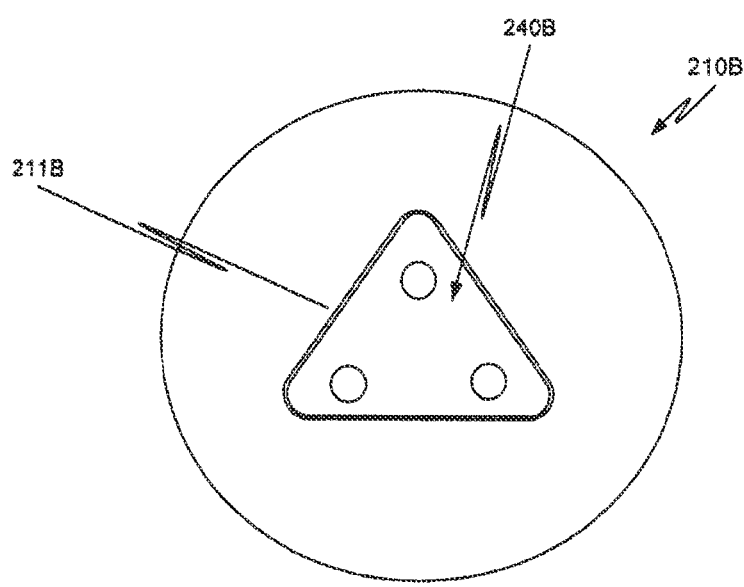
FIG. 2B is a cross sectional view of a tether and a shape sensor having a second non-circular cross section.

For example, in FIG. 2A, torsionally stiff body 210A has a lumen with a non-circular cross section 211A, and shape sensor 240A has an equivalent non-circular cross section. In FIG. 2B, torsionally stiff body 210B has a lumen with a rounded triangular cross section 211B, and shape sensor 240B has an equivalent rounded triangular cross section.

The cross sections in FIGS. 2A and 2B are illustrative only and are not intended to limiting. When the cross sectional shape of the shape sensor is known, a lumen with substantially the same cross sectional shape can be formed in the torsionally stiff tether. For example if the cross section of the shape sensor is a letter D shape, the cross section of the lumen in the tether would have a letter D shape.

In another aspect, twisting of shape sensor 140 is mitigated by enclosing shape sensor 140 in low-friction tubing so that shape sensor 140 rotates freely within the lumen of the tubing and does not twist beyond the threshold irrespective of any twist in the tubing. The low-friction tubing is passed through the lumens in the tether and in the surgical instrument.

As an example, the low-friction tubing is made from a fluorinated polymer. One example of a fluorinated polymer is polytetrafluoroethylene (PTFE).

Alternatively, a torsionally stiff body can be used in combination with low-friction tubing inserted in the lumen of the torsionally stiff body. Irrespective of whether a torsionally stiff tether body is used, low-friction tubing is used in a lumen of the tether, or a combination of the two is used, the shape sensor remains substantially twist free. Herein, substantially twist free means that the twist of the shape sensor is less than the threshold described above for the torsionally stiff tether.

Figure 3:
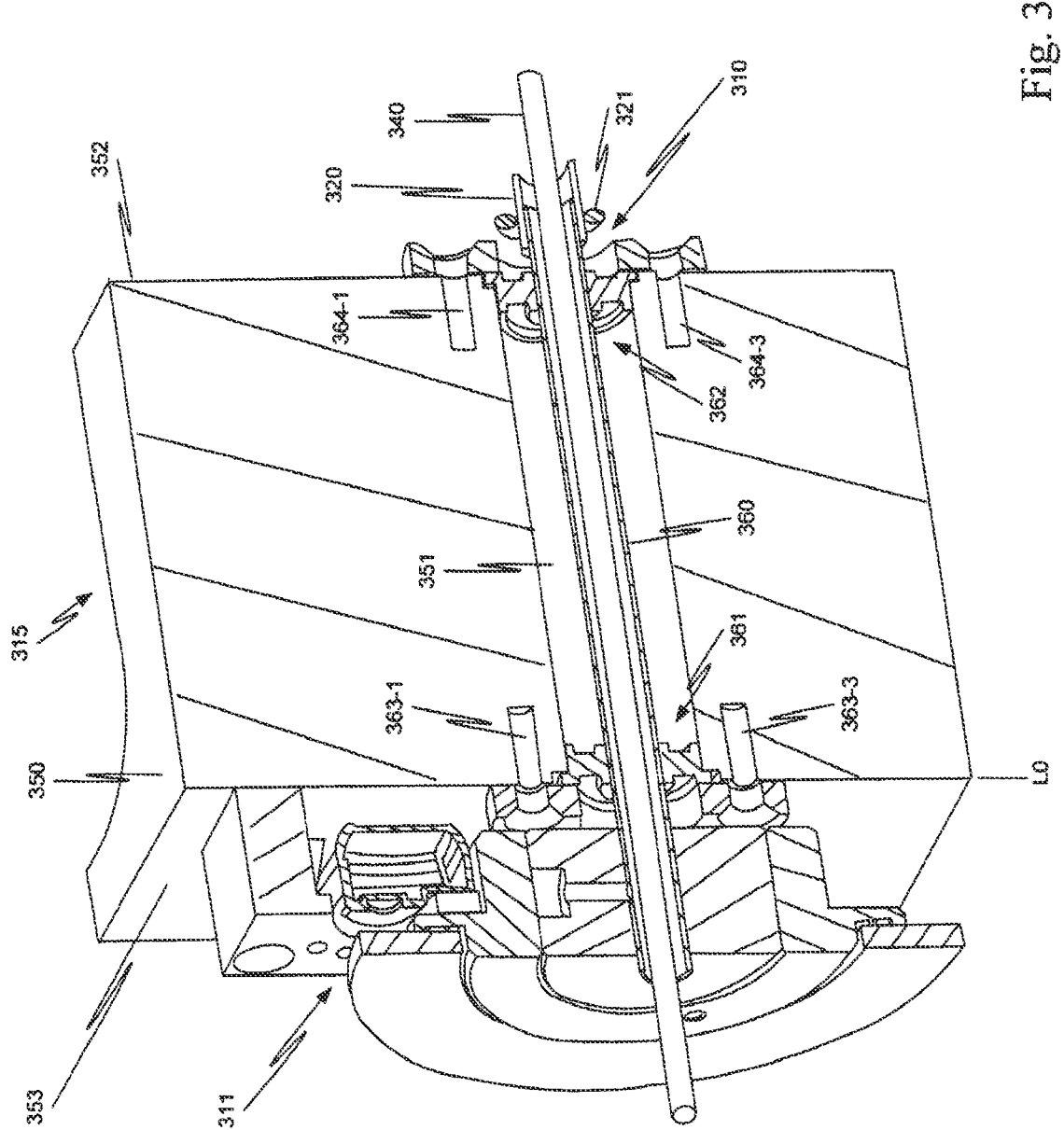
FIG. 3 is a perspective cross sectional view of one aspect of a reference fixture.

FIG. 3 is a perspective cross-sectional view of one example of a reference fixture 315. A body 350 of reference fixture 315 has a lumen 351 extending through body 350 from a first edge surface 352 to a second edge surface 353. Body 350 also includes a plurality of threaded screw holes extending into body 350 from first edge surface 352, and from second edge surface 353. In FIG. 3, threaded screw holes 363-1, 363-3, 364-1, 364-3 in the plurality of threaded screw holes are visible. The plurality of screw holes is used to attach roll joint 310 to body 350.

Roll joint 310 includes a first bearing 361 and a second bearing 362 mounted in lumen 351. First and second bearings 361, 362 support a hollow rod 360 that passes through lumen 351. Hollow rod 360 extends beyond first edge surface 352.

Tether 320 is connected to the end of hollow rod 360 extending beyond first edge surface 352 by a clamp 321. Thus, roll motion of the proximal end of tether 320 is transferred to rod 360.

Hollow rod 360 also extends beyond second edge surface 352 and passes through a lumen in roll joint tracker 311 that is affixed to hollow rod 360. Thus, as rod 360 turns, the roll motion is transferred to roll joint tracker 311 and is measured by roll joint tracker 311. Roll joint tracker 311 is a conventional optical joint tracker and so is known to those knowledgeable in the field.

Use of an optical joint tracker is illustrative only and is not intended to be limiting. Upon selection of a joint or joints, appropriate tracking mechanisms can be selected. If the joint has no degrees of freedom, the joint tracker is not used.

Shape sensor 340 passes through hollow rod 360 and is fixed in position after shape sensor 340 passes out of the end of rod 360 adjacent to roll joint tracker 311. Shape sensor 340 is fixed in position as described above.

In the example of FIG. 3, a single degree of freedom is restrained by fixture 315. In other implementations, additional degrees of freedom can be restrained by the reference fixture to improve the manipulability of the surgical instrument.

The ability to obtain three-dimensional shape and pose measurements in a fixed world reference frame enhances the capabilities available for minimally invasive surgical procedures. Two examples are considered. In a first example, a minimally invasive teleoperated surgical system and a laparoscopic system are used in combination. In a second example, only a laparoscopic system is considered.

The first example includes a conventional minimally invasive teleoperated surgical system, such as the da Vinci' Surgical System, manufactured by Intuitive Surgical, Inc., Sunnyvale, California, and utilizes internal system knowledge that the system has about itself. The second example is a totally laparoscopic version which gathers all information directly with a laparoscopic positioning system.

Figure 4A:
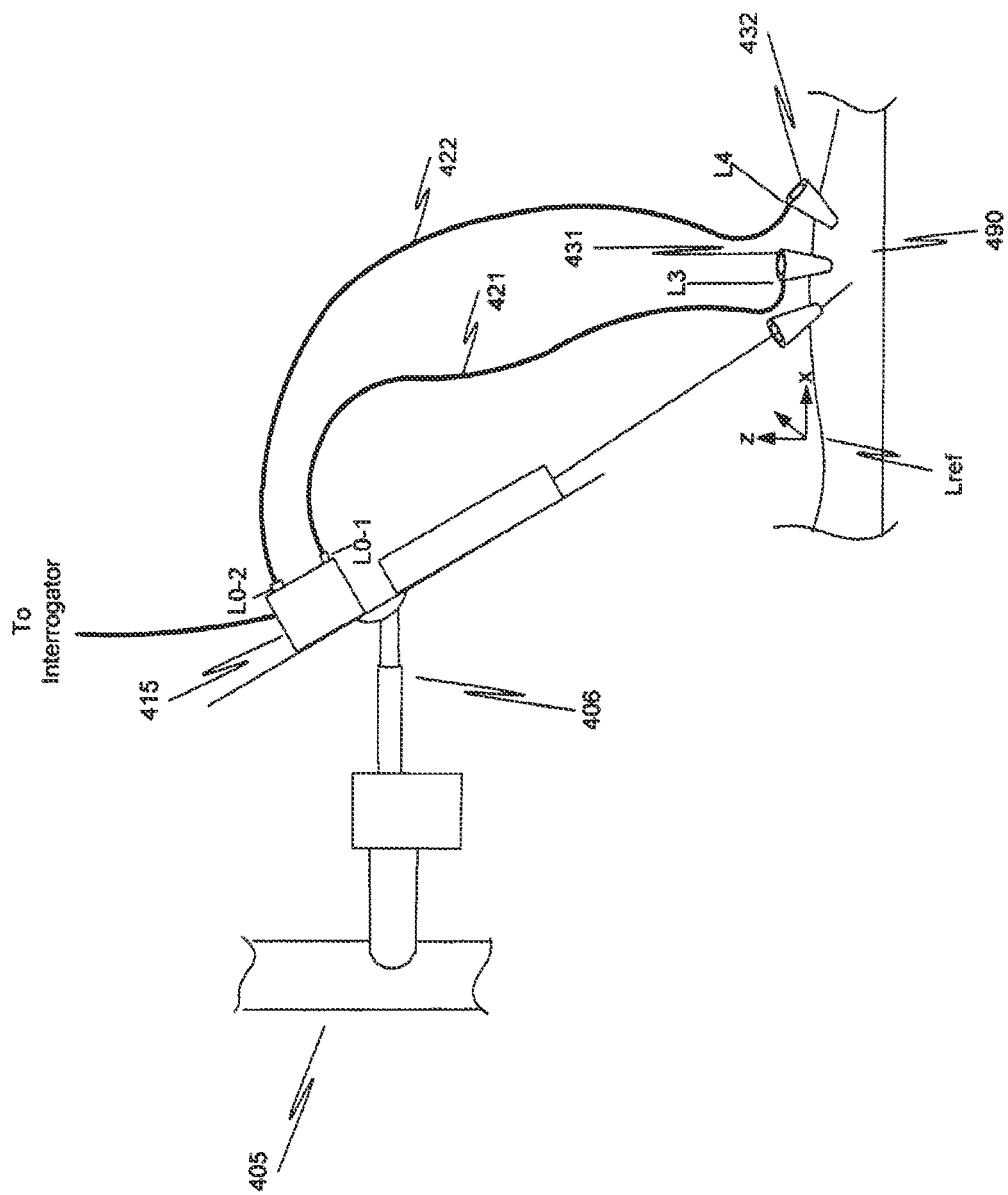
FIG. 4A is a diagrammatic view of a portion of a minimally invasive teleoperated surgical system, which includes elements to generate absolute three-dimensional pose, in a fixed world reference frame, for a plurality of surgical instruments.

In the first example with the minimally invasive robotic surgical system, only a portion of the system is illustrated in FIG. 4A. A cart 405 supports a plurality of manipulators. In this example, an endoscopic camera manipulator 406 is illustrated.

A reference fixture 415, mounted on endoscopic camera manipulator 406, is similar to reference fixture 115 except reference fixture 415 is connected to a plurality of tethers, which in this example includes tether 421 and tether 422. Again, in this example, the fixed world reference frame at location Lref is defined at a location on patient 490. A reference frame for the shape sensor passing through tether 421 is defined at location LO-1 and a reference frame for the shape sensor passing through tether 422 is defined at location LO-2.

In a manner similar to that described above with respect to FIG. 1, the pose in the reference frame at location LO-1 is mapped by controller 180 into the fixed world reference frame at location Lref. Similarly, the pose in the reference frame at location LO-2 is mapped by controller 180 into the fixed world reference frame at location Lref.

In this example, the shape sensor passing through tether 421 has a known feature, such as an S-curve, after leaving tether 421 and entering cannula 431. Similarly, the shape sensor passing through tether 423 has a known feature after leaving tether 422 and entering cannula 432. Cannulas 431, 432 are examples of a particular surgical instrument.

In this example, reference fixture 415 includes a first joint tracker that tracks motion of the joint connected to tether 421 that in turn is connected to cannula 431, and a second joint tracker that tracks motion of the joint connected to tether 422 that in turn is connected to cannula 432.

However, in some aspects, even though the tether is torsionally stiff, manipulability of the surgical instrument may be adequate without providing a joint with any degrees of freedom in the reference structure. For example, a cannula may be sufficiently movable when attached to a torsionally stiff tether that a one-degree of motion joint is not needed. In this situation, the joint in the reference structure has zero degrees of freedom and the joint tracker is not used.

The known feature of the shape sensor in cannula 431 provides information that is processed to determine the pose of cannula 431, at location L3. The integration described more completely below of information from shape sensor 140 is performed from location LO-1 to location L3 to generate pose information for a frame at location L3, in the reference frame at location LO-1. Combining this with the pose of the reference frame at location LO-1 generates pose information for the frame at location L3 in the fixed world reference frame at location Lref. The process is the same as that described above with respect to FIG. 1. An equivalent process is used to obtain the three-dimensional pose of cannula 432, at location L4, in the fixed world reference frame at location Lref.

Three-dimensional pose information for the manipulator on which reference fixture 415 is mounted is known internally within the minimally-invasive surgical system. Thus, the pose information generated in the fixed world reference frame for cannulas 431, 432 can be mapped into the reference frame for the manipulator.

Figure 4B:
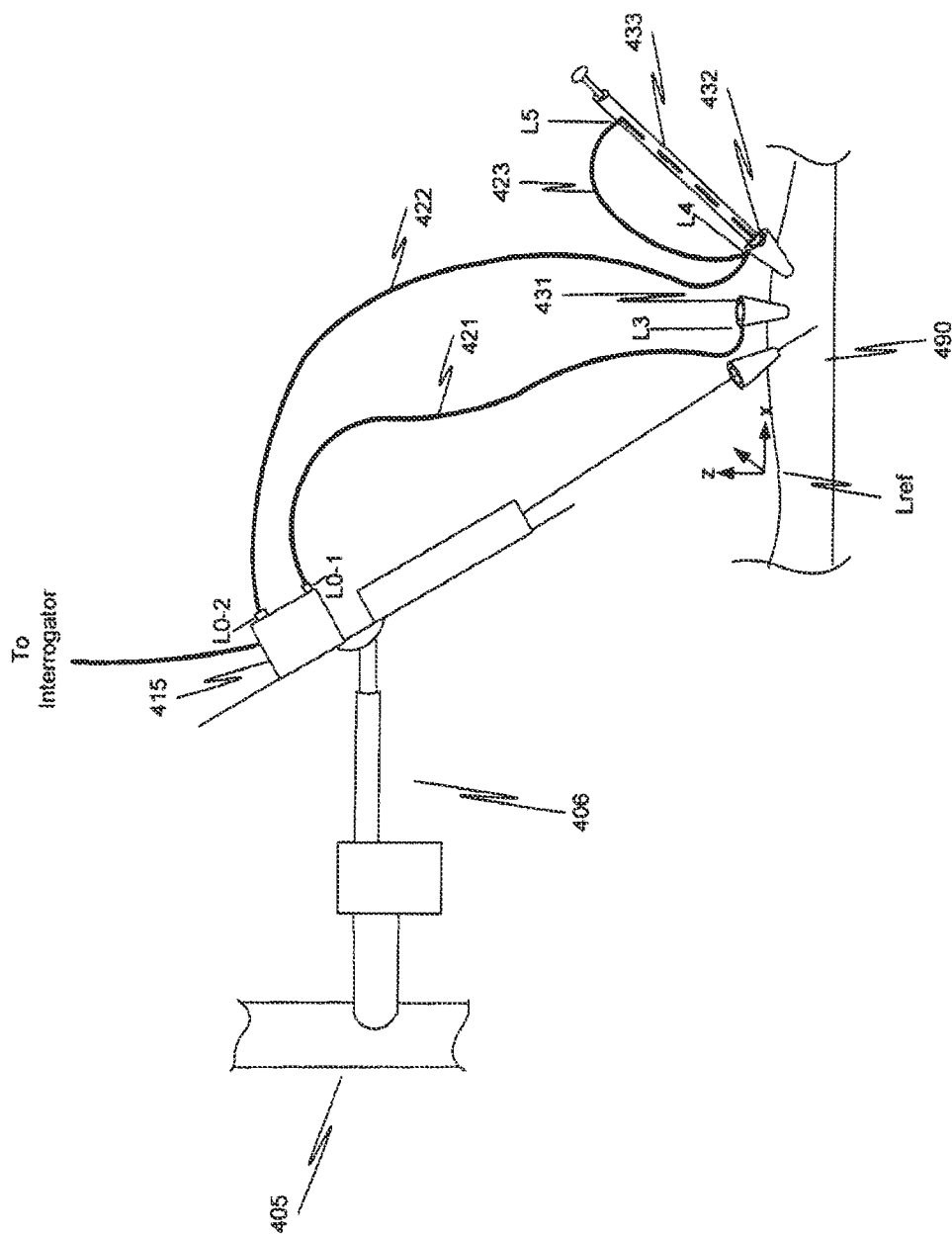
FIG. 4B is a diagrammatic view of a portion of a minimally invasive teleoperated surgical system, which includes elements to generate absolute three-dimensional pose and shape data, in a fixed world reference frame, for another plurality of surgical instruments.

An insertion depth of a manually inserted surgical instrument 433 (FIG. 4B) is directly measured by the addition of a second tether 423 between tethered cannula 432 and surgical instrument 433. The shape sensor extends through location LO-2 through tether 422 to cannula 432 and from cannula 432 through tether 423 to a known feature in surgical instrument 433. In the example of FIG. 4B, the pose at location L5 in the fixed world reference frame at location Lref and the pose at location L4 in the fixed world reference frame at location Lref are used to determine the insertion depth. The distance between the poses for the two locations diminishes as instrument 433 is inserted.

A system utilizing a minimally invasive teleoperated surgical coupled system has a significant advantage in that the reference to the camera can make use of state variables that are known to the system such as camera angle, depth of insertion of the camera tip and focus depth. In a laparoscopic system only, all of the variables must be directly measured.

Direct measurement of all of cannula positions with tethers back to the same reference point can establish the vector of the instrument cannulas with respect to the camera cannula in a manner equivalent to that described above. The depth of the scope insertion can be measured with an additional tether as described above.

As described above, in one aspect, the shape sensor is implemented using a multi-core optic fiber with Bragg Fiber Gratings. In one example, the optic fiber is a three core optic fiber, as described more completely below. In other embodiments, various numbers of cores may be used.

In this example, interrogator 170 interrogates the optic fiber and provides shape information from the optic fiber to an input/output module 181 in controller 180. Interrogator 170 implements Optical Frequency Domain Refleotometry technology with a standard Optic Backscatter Reflectometer for each core in the optic fiber.

The shape information is analyzed as a function of a discretized curvilinear coordinate S(t). A processor in a processor module 182 of controller 180 executes computer instructions in a shape information processing module 184 stored in memory 183. The processor determines the reference frame at location LO. The processor then performs an integration from the location of the reference frame at location LO to the geometrical center of the known feature at location L1. In one aspect, the location of the geometrical center of the known feature is determined by finding the center of the shape signature representing the known feature.

The integration (See expression (15) below) generates the x-y-z position and orientation of the known feature at location L1, which in turn can be used to determine the position and angle of the geometrical center of the known feature relative to the fixed world reference frame at location Lref.

A more detailed description of one process used to obtain coordinates $(x_n, y_n, z_n)$ at curvilinear coordinate LO+S1 is described in copending and commonly assigned U.S. Patent Application Publication No. US 2009/0324161 A1, which was previously incorporated herein by reference in its entirety.

Figure 5:
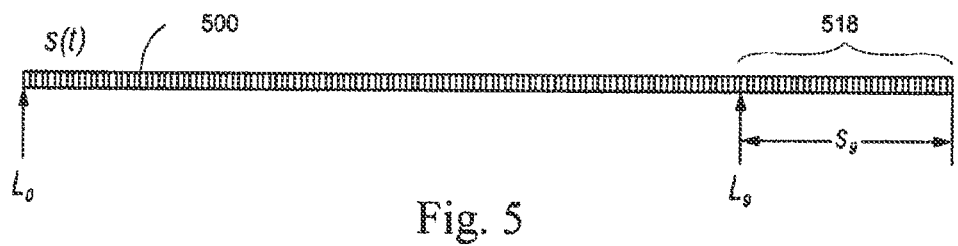
FIG. 5 is a diagrammatic view of an optic fiber core.

FIG. 5 is a diagrammatic view of one configuration of an optic fiber core 500. Other configurations are illustrated in copending and commonly assigned U.S. Patent Application Publication No. US 2009/0324161 A1.

In. FIG. 5, the surrounding cladding and fiber are omitted for clarity. Each of the many vertical lines shown represents individual, adjacent Fiber Bragg Gratings. As described below, each core is one core of three or more cores in a single optic fiber.

As indicated above and shown in FIG. 5, a curvilinear coordinate system S(t) is defined for the fiber, and hence for core 500 and the other cores (not shown). In some cases, location LO of the origin of coordinate system S(t) is defined relative to fixture 115, as described above.

Once origin location LO is defined, one or more shape-sensing segments are defined between locations along the core. Each defined shape-sensing segment of a core contains part of one Fiber Bragg Grating, or one full Fiber Bragg Grating, or many adjacent Fiber Bragg Gratings. As shown in FIG. 5, core 500 has Fiber Bragg Gratings defined along its entire length, with shape sensing segment 518 defined at the distal end of the core, with no additional segments defined in the Fiber Bragg Grating-configured core. Shape-sensing segment 518 starts at location $L_9$ and extends for a distance $S_9$.

Figure 6:
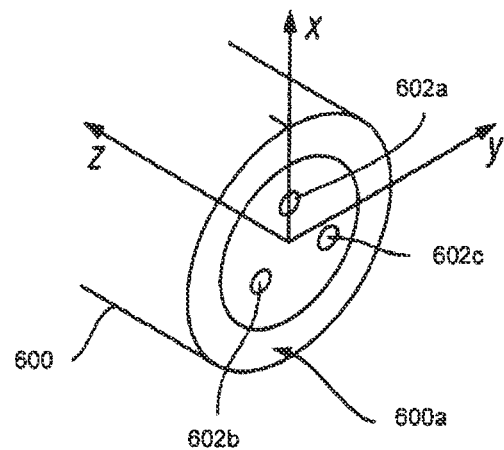
FIG. 6 is a diagrammatic view of the proximal end of an optic fiber with an illustrative reference frame.

FIG. 6 is a diagrammatic view of the proximal end of an optic fiber 600 with an illustrative reference frame defined.

As shown in FIG. 6, fiber 600 has three Fiber Bragg Grating-configured cores 602a, 602b, 602c within a cladding layer 600a. Each core 602a, 602b, 602c is positioned at an apex of an equilateral triangle centered in optic fiber 600.

As shown in FIG. 6, a Cartesian reference frame is defined for optic fiber 600. One axis of the Cartesian reference frame intersects one of the cores (the x-axis is shown intersecting core 602a as an illustration) and another axis is tangent to the centerline of optic fiber 600 (the z-axis is shown as an illustration). Defining the x-axis to extend through a core provides a rotational reference around the centerline of optic fiber 600. The definition of the x-axis is arbitrary and can be based on the geometry of the kinematic chain embedding the optic fiber. For instance, the x-axis could be aligned to one joint axis of the kinematic chain in which the optic fiber is embedded or associated.

The Cartesian reference frame (x, y, z) shown in FIG. 6 functions as a base frame when defined with an origin coincident with the origin of the curvilinear coordinate system S(t). When a Cartesian reference frame is defined with an origin at a segment start location, the Cartesian reference frame functions as a shape-sensing segment reference frame. A Cartesian reference frame may be similarly defined at a segment end location. Although three cores are shown in FIG. 6, other numbers of cores may be used (e.g., two opposite cores for planar bend measurement, four cores to measure fiber twist, etc.).

Figure 7:
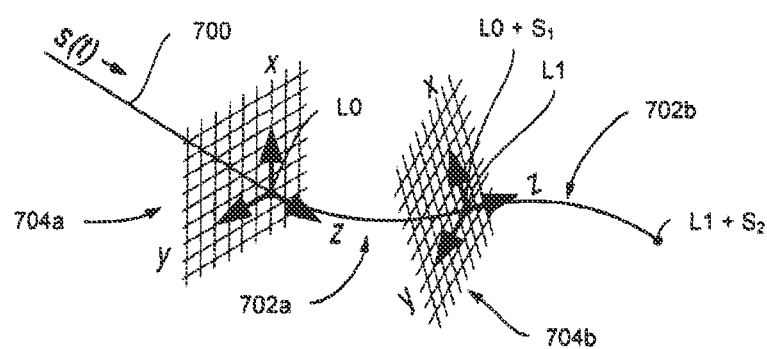
FIG. 7 is a diagrammatic view that illustrates reference frames at segment start locations in an optical fiber used for shape sensing.

FIG. 7 is a diagrammatic view that illustrates reference frames at segment starts in an optical fiber used for shape sensing. FIG. 7 depicts an optical fiber 700 that is, in one embodiment, configured with three cores as illustrated in FIG. 6 (four cores or other core configurations may be used). Two shape-sensing segments are defined in optic fiber 700. A first segment 702a is defined from curvilinear reference location LO (segment start) to curvilinear reference location LO+$S_1$ (segment end). The second segment 702b is defined from curvilinear reference location L1 (segment start) to curvilinear reference location L1+$S_2$ (segment end). In accordance with an aspect of the invention, a first Cartesian reference frame 704a is defined at segment start LO. The z-axis of reference frame 704a is tangent to the centerline of optic fiber 700 at segment start LO. The x-axis of reference frame 704a runs through one of the cores as illustratively shown and described in FIG. 6. Similarly, a second Cartesian reference frame 704b is defined at segment start L1, with the z-axis of reference frame 704b tangent to the centerline of optic fiber 700 at segment start L1. The x-axis of reference frame 704b runs through the same core the x-axis of reference frame 704a.

The base reference frame illustrated in FIG. 6 and the two segment start reference frames illustrated in FIG. 7 are interrelated because all three have one normal axis (e.g., the x-axis) defined through the same core (e.g., core 702a).

The following is an illustration of computations carried out by an electronic data processing unit, sometime simply call a processor, in controller 180. Skilled individuals will understand that many hardware, firmware, and software options exist for constructing an electronic data processing unit, and that implementation of necessary computations will be routine in light of this description.

The expression for the local strain e(J) is written as a function of distance along a given fiber core, $$\varepsilon_n = \varepsilon(\Delta dn) \tag{1}$$

where $\Delta d$ is the distance increment per index n The $\Delta d$ value is set by the resolution of the OFDR-based interrogator. For instance the local strain ε(s) as a function of distance along each fiber core is obtained by making use of an "Optical Backscatter Reflectometer", a commercially available product from Luna Innovations Incorporated, Roanoke, Virginia, for each core. Such a device is able to output the phase derivative of the reflected light as a function of the distance along the fiber core, as shown in *Optical Backscatter Reflectometer User Guide* Chaps 5-6, 33-60 (Luna Technologies, Inc. 2004) (Document version 1.0 for OBR control software version 0.42 Beta), which is incorporated herein by reference. Such Phase Derivative information is proportional to the desired local strain ε(S) in expression (1).

For the pre-set perturbation, the differential strains between the cores are needed. For three cores, the required differential strains are:

$$\Delta \varepsilon_{p,n} = \varepsilon_{2,n} - \varepsilon_{1,n} \tag{2a}$$

$$\Delta \varepsilon_{q,n} = \varepsilon_{3,n} - \varepsilon_{1,n} \tag{2b}$$

where $\Delta \varepsilon_p$ and $\Delta \varepsilon_q$ designate the two differential strain arrays.

These differential strains can then be converted into local bends in an ortho-normal coordinate system by using a simple linear transformation.

$$\begin{bmatrix} \theta_{x,n} \\ \theta_{y,n} \end{bmatrix} = \begin{bmatrix} m_{px} & m_{qx} \\ m_{py} & m_{qy} \end{bmatrix} \begin{bmatrix} \Delta \epsilon_{p,n} \\ \Delta \epsilon_{q,n} \end{bmatrix} \tag{3}$$

The m-matrix $\overline{m}$ is a full description of the multi-core fiber, capturing the effects of the locations of the cores and the initial rotational orientation of the fiber in the coordinate system.

Next, these two rotation values are used to create a rotation matrix equal to the product of a first rotation of an angle $\theta_{x,n}$ around the x-axis and a second rotation of $\theta_{y,n}$ around the y-axis according to the equations:

$$\overline{R}_{x,n} = \begin{bmatrix} 1 & 0 & 0 \\ 0 & \cos\theta & -\sin\theta \\ 0 & \sin\theta & \cos\theta \end{bmatrix} \tag{4}$$

$$\overline{R}_{y,n} = \begin{bmatrix} \cos\theta & 0 & \sin\theta \\ 0 & 1 & 0 \\ -\sin\theta & 0 & \cos\theta \end{bmatrix}$$

$$\overline{R}_n = \overline{R}_{x,n} \, \overline{R}_{y,n}$$

For a small angle approximation, the above expression simplifies to:

$$\overline{R}_n = \begin{bmatrix} 1 & 0 & \theta_{y,n} \\ 0 & 1 & -\theta_{x,n} \\ -\theta_{y,n} & \theta_{x,n} & 1 \end{bmatrix} \tag{5}$$

where, because a first order small angle approximation is used, $\overline{R}_n$ is a valid rotation matrix only if $\theta_x \ll 1$ and $\theta_y \ll 1$.

If sufficiently small spatial increments are used, the above conditions are not difficult to satisfy. This rotation matrix is then moved into the coordinate system at the $n^{th}$ position on the fiber. In this way, the calculations are iterated to walk down the length of the fiber, reconstructing the tangent vector, as well as the vectors defining the rotational coordinate system, along the way. The iterative equation is, $$\overline{\overline{C_{n+1}}} = \overline{\overline{C_n R_n}} \tag{6}$$

Or, when using the small-angle approximation, $$\begin{bmatrix} c_{11} & c_{12} & c_{13} \\ c_{21} & c_{22} & c_{23} \\ c_{31} & c_{32} & c_{33} \end{bmatrix}_{n+1} = \begin{bmatrix} c_{11} & c_{12} & c_{13} \\ c_{21} & c_{22} & c_{23} \\ c_{31} & c_{32} & c_{33} \end{bmatrix}_n \begin{bmatrix} 1 & 0 & \theta_y \\ 0 & 1 & -\theta_x \\ -\theta_y & \theta_x & 1 \end{bmatrix}_n \tag{7}$$

And so, the coordinate system at any location along the array is given by, $$\overline{\overline{C}}_p = \overline{\overline{C}}_o \overline{\overline{R}}_o \overline{\overline{R}}_1 \overline{\overline{R}}_2 \cdots \overline{\overline{R}}_p = \overline{\overline{C}}_o \prod_{n=0}^{p} \overline{\overline{R}}_n \tag{8}$$

The initial value of this coordinate system matrix, $$\overline{\overline{C}}_o = \begin{bmatrix} c_{11} & c_{12} & c_{13} \\ c_{21} & c_{22} & c_{23} \\ c_{31} & c_{32} & c_{33} \end{bmatrix}_0 \tag{9}$$

Describes the initial orientation of the fiber in the exterior coordinate system. If the fiber is initially aligned along the z-axis, the matrix will be, $$\overline{\overline{C}}_o = \begin{bmatrix} \sin\beta & -\cos\beta & 0 \\ \cos\beta & \sin\beta & 0 \\ 0 & 0 & 1 \end{bmatrix}_0 \tag{10}$$

In the description above, the first two vectors still have one degree of freedom, which is the rotation of the fiber around its axis—the same rotational degree of freedom in the m-matrix above. In many implementations, this situation is not generally a problem, because it will generally be taken care of automatically by the way the fiber is embedded in or associated with the kinematic chain and by calibration. Further, it means that complete generality can be retained even if the initial matrix is restricted to be, $$\overline{\overline{C}}_o = \begin{bmatrix} 1 & 0 & 0 \\ 0 & 1 & 0 \\ 0 & 0 & 1 \end{bmatrix}_0 \tag{11}$$

The tangent vector $\bar{t}$ is the last column of the $\overline{\overline{C}}$ matrix, $$\bar{t} = \overline{\overline{C}} \cdot \begin{bmatrix} 0 \\ 0 \\ 1 \end{bmatrix} \tag{12}$$

Accordingly, the tangent vector at any particular point is the product of all of the previous rotation vectors, $$\bar{t}_p = \overline{\overline{C}}_o \prod_{n=0}^{p} \overline{\overline{R}}_n \cdot \begin{bmatrix} 0 \\ 0 \\ 1 \end{bmatrix} \quad (13)$$

The position at any point along the fiber is the sum of all of the previous tangent vectors, multiplied by the length of fiber that they represent, $$\begin{bmatrix} x \\ y \\ z \end{bmatrix}_q = \Delta d \sum_{p=0}^{q} \bar{t}_p \quad (14)$$

Substituting in the expression for the tangent vector gives, $$\begin{bmatrix} x \\ y \\ z \end{bmatrix}_q = \Delta d \sum_{p=0}^{q} \left[ \left\{ \overline{\overline{C}}_o \prod_{n=0}^{p} \overline{\overline{R}}_n \right\} \cdot \begin{bmatrix} 0 \\ 0 \\ 1 \end{bmatrix} \right] \quad (15)$$

For generality, an arbitrary offset vector can be added to place the calculated coordinates into any arbitrary coordinate system.

$$\begin{bmatrix} x \\ y \\ z \end{bmatrix}_q = \Delta d \sum_{p=0}^{q} \left[ \left\{ \overline{\overline{C}}_o \prod_{n=0}^{p} \overline{\overline{R}}_n \right\} \cdot \hat{z} \right] + \bar{v}_0 \quad (16)$$

where, $$\bar{v}_0 = \begin{bmatrix} x_0 \\ y_0 \\ z_0 \end{bmatrix} \quad (17)$$

and, $$\hat{z} = \begin{bmatrix} 0 \\ 0 \\ 1 \end{bmatrix} \quad (18)$$

For the computation of the position and orientation of the frame of reference at the end of a segment with respect to the frame of reference at the start of the segment, $\overline{\overline{C}}_O$ is the identity matrix, and $\bar{v}_0$ is a vector of zeros, which represents the frame of reference at the start of the segment. Alternatively, the computation can be carried in another base or world frame located, for instance, at the base of the kinematic chain. In this case $\overline{\overline{C}}_O$ is the 3×3 matrix specifying the orientation of the frame of reference at the start of the segment with respect to the above-mentioned base frame, and $\bar{v}_0$ is the 3×1 vector specifying the position of the origin of the frame of reference at the start segment with respect to the above-mentioned base frame.

As mentioned above, in some instances the quantity Δd is known from the property of the particular interferometer that is used. Alternatively, Δd can be calibrated by laying the segment of fiber in a straight line, for instance with the use of a fixture, and comparing the computed segment tip position from equation 18 with the known segment physical length.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

As used herein, a Fiber Bragg Grating comprises a series of modulations of a core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the Fiber Bragg Gratings, the modulations are spaced by a known distance, thereby causing reflection of a known band of wavelengths. However, when a strain is induced on the fiber core, the spacing of the modulations will change, depending on the amount of strain in the core.

Further, this description's terminology is not intended to limit the invention. For example, spatially relative terms—such as "beneath", "below", "lower", "above", •upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

While the memory in FIG. 1 is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the operations described with respect to the shape information processing module or in which computer readable code for any one or any combination of operations described with respect to the shape information processing module is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible medium configured to store computer readable instructions for any one of, or any combination of operations described with respect to the shape information processing module or in which computer readable instructions for any one of, or any combination of operations described with respect to the shape information processing module are stored. Non-transitory tangible computer program products are CD-ROM discs, DVD discs, flash memory, ROM cards, floppy discs, magnetic tapes, computer hard drives and other non-transitory physical storage mediums.

In view of this disclosure, instructions used in any one of, or any combination of operations described with respect to the shape information processing module can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A system comprising:
   a teleoperated manipulator;
   a manually operated instrument;
   a position sensor coupled to the manually operated instrument, the position sensor being configured to generate pose information for the manually operated instrument; and
   a controller configured to:
      map a pose of the manipulator to a fixed world reference frame based on three-dimensional pose information for the manipulator known internally within the system, wherein the three-dimensional pose information is determined independent of the pose information generated by the position sensor and is determined utilizing internal system knowledge determined independent of the pose information generated by the position sensor; and
      map a pose of the manually operated instrument to the fixed world reference frame based on the pose information for the manually operated instrument.

2. The system of claim 1, wherein the controller is further configured to map the pose of the manually operated instrument in the fixed world reference frame to a reference frame of the manipulator.

3. The system of claim 2, wherein the controller is configured to map the pose of the manually operated instrument in the fixed world reference frame to the reference frame of the manipulator based on the three-dimensional pose information for the manipulator known internally within the system.

4. The system of claim 1, wherein the manipulator comprises an endoscopic camera manipulator.

5. The system of claim 1, wherein the manually operated instrument is coupled to the teleoperated manipulator by a tether.

6. The system of claim 1, wherein the controller is further configured to measure movement of the manually operated instrument by using the pose information for the manually operated instrument.

7. The system of claim 6, wherein measuring the movement of the manually operated instrument includes measuring an insertion depth or an orientation of the manually operated instrument.

8. The system of claim 7, wherein the orientation of the manually operated instrument includes rotation of the manually operated instrument.

9. The system of claim 1, wherein the controller is further configured to:
   map a second pose of the manually operated instrument to the fixed world reference frame based on second pose information for the manually operated instrument generated from the position sensor; and
   measure movement of the manually operated instrument by using the pose information and the second pose information for the manually operated instrument mapped to the fixed world reference frame.

10. The system of claim 1, further comprising a cannula comprising a cannula opening at a proximal end of the cannula, wherein the manually operated instrument is configured to be inserted into the cannula opening.

11. The system of claim 1, further comprising a reference fixture coupled to the manipulator, wherein the reference fixture moves with the manipulator.

12. A method performed by a controller of a teleoperated system, the method comprising:
   mapping a pose of a teleoperated manipulator to a fixed world reference frame based on three-dimensional pose information for the manipulator; and
   mapping a pose of a manually operated instrument to the fixed world reference frame based on pose information for the manually operated instrument generated from a position sensor coupled to the manually operated instrument,
   wherein the three-dimensional pose information is determined independent of the pose information generated by the position sensor and is determined utilizing internal system knowledge determined independent of the pose information generated by the position sensor.

13. The method of claim 12, further comprising:
mapping the pose of the manually operated instrument in the fixed world reference frame to a reference frame of the teleoperated manipulator.

14. The method of claim 13, wherein the mapping of the pose of the manually operated instrument in the fixed world reference frame to the reference frame of the manipulator is based on the three-dimensional pose information for the manipulator.

15. The method of claim 12, further comprising:
measuring movement of the manually operated instrument by using the pose information for the manually operated instrument.

16. The method of claim 15, wherein measuring the movement of the manually operated instrument includes measuring an insertion depth or an orientation of the manually operated instrument.

17. The method of claim 16, wherein the orientation of the manually operated instrument includes rotation of the manually operated instrument.

18. The method of claim 16, wherein measuring the insertion depth of the manually operated instrument includes measuring the insertion depth as the manually operated instrument is inserted through a cannula opening at a proximal end of a cannula.

19. The method of claim 12, further comprising:
mapping a second pose of the manually operated instrument to the fixed world reference frame based on second pose information for the manually operated instrument generated from the position sensor; and
measuring movement of the manually operated instrument by using the pose information and the second pose information for the manually operated instrument mapped to the fixed world reference frame.

20. The method of claim 12, further comprising receiving the pose information for the manually operated instrument from a position sensor coupled to the manually operated instrument.

21. The system of claim 1, wherein the internal system knowledge comprises position information for one or more joints of the teleoperated manipulator, the position information determined at least partially from encoder data corresponding to the one or more joints.

* * * * *